United States Patent [19]

Hunter

[11] 4,125,375
[45] Nov. 14, 1978

[54] SEPARATION OF SOLID AND LIQUID COMPONENTS OF MIXTURES

[75] Inventor: William M. Hunter, Edinburgh, Scotland

[73] Assignee: National Research Development Corporation, London, England

[21] Appl. No.: 740,485

[22] Filed: Nov. 10, 1976

[30] Foreign Application Priority Data

Nov. 14, 1975 [GB] United Kingdom ............... 47078/75

[51] Int. Cl.² ............................................ G01N 33/16
[52] U.S. Cl. .................................. 23/230 B; 23/230.3; 128/DIG. 5; 210/83; 210/143; 210/221 R; 424/1
[58] Field of Search .......................... 210/83, 141–143, 210/148, 221 R, 511; 128/DIG. 5; 424/1; 23/230 B, 230.3

[56] References Cited

U.S. PATENT DOCUMENTS

| 2,833,618 | 5/1958 | Creutz et al. | 210/83 X |
| 3,682,305 | 8/1972 | Buchler | 210/83 |
| 3,752,758 | 8/1973 | Elhindi et al. | 210/83 X |
| 3,788,812 | 1/1974 | Dupre | 424/1 X |
| 3,950,643 | 4/1976 | Charlton | 424/1 X |
| 4,033,866 | 7/1977 | Enzmann | 210/511 |

Primary Examiner—William A. Cuchlinski, Jr.
Attorney, Agent, or Firm—Oblon, Fisher, Spivak, McClelland & Maier

[57] ABSTRACT

A method of separating solid and liquid components of mixtures comprises delivering to the mixture a second liquid, having a density intermediate between those of the solid and liquid components of the mixture, to form a discrete layer above or below the mixture, and allowing the solid to separate into the layer of the second liquid, especially for use in automated analytical systems e.g. automated radioimmunoassay systems. There is also included automated apparatus for delivery of the second liquid of intermediate density and removal of supernatant liquid subsequent to separation.

15 Claims, 4 Drawing Figures

SEPARATION OF SOLID AND LIQUID COMPONENTS OF MIXTURES

This invention relates to the separation of solid and liquid components of mixtures and in particular to a technique for use in automated systems for the separation of solids from liquids.

In recent years a wide range of automatic analytical equipment has become available for use in the industrial and, in particular, clinical fields, and includes automated radio-immunoassay (RIA) systems. RIA and other binding assays techniques have acquired immense importance in clinical practice, where they have made a major contribution to present day understanding of endocrinology.

Many analytical procedures, however, require the separation of solid and liquid components of mixtures and such separations, owing to their inherent unsuitability, are difficult to automate. For example, it has been proposed (Butler, Bagshawe et al pp 635–638 "Radioimmunoassay methods" Ed. Kirkham and Hunter, pub. Churchill Livingstone, Edinburgh, 1971), in an automated RIA system to effect this separation by an automated filtration step. Filtration however is not readily adapted to automation and leads to unavoidable mechanical complexity and thus expense, and also, of necessity, involves contact of the mixture being filtered with extraneous surfaces which can lead to loss of material and inaccuracies in the results obtained.

An improved method of separating solid and liquid components of mixtures has now been devised particularly suited for use in automated systems and which also diminishes contact with extraneous surfaces.

According to the present invention a method of separating solid and liquid components of mixtures comprises delivering to the mixture a second liquid, having a density intermediate between those of the solid and liquid components of the mixture, to form a discrete layer above or below the mixture, and allowing the solid to separate into the layer of the second liquid.

Normally the solid component of the mixture is more dense than the liquid component. Thus more usually the invention comprises delivering to the mixture a second liquid, having a density intermediate between those of the solid and liquid components of the mixture, to form a discrete layer beneath the mixture, and allowing the solid to separate into the lower layer of the second liquid. Conveniently the solid may be allowed to separate under the action of gravity into the lower liquid layer, though advantageously additional applied force may be employed to enhance the rate of separation. For instance, centrifugal force may be employed to assist separation of the solid into the lower liquid layer or alternatively a magnetic field may be used when the solid phase comprises ferromagnetic material (e.g. in the manner of Nye et al Clin. Chem. Acta 1976, 69 (3) at page 387). Generally the use of applied force may assist in the removal of supernatant liquid contamination from the solid.

It will be appreciated that the method of the present invention is widely applicable to the separation of solid and liquid components of mixtures in general. More particularly however, the method finds advantageous application as a separation technique for use in automated systems and especially automated analytical systems such as automated binding assays e.g. RIA systems. Such automated analytical systems include both discrete sample and continuous flow systems. Without prejudice to the wider application of the invention, the present description however concentrates upon application of this method as a separation technique for use in binding assays.

Binding assay techniques typically depend upon an immunological reaction in which an antigen or hapten, reacts with an antiserum. Generally the techniques rely upon competitive binding of the substance being assayed and a labelled e.g. radio-labelled, version of that substance, subsequent to which the bound and free fractions are separated so that the ratio of labelled component in the two fractions may be determined. In an alternative method the binding reagent itself may instead be labelled. Thus the method of the present invention may be applied to systems in which the bound and free fractions are in the form of a solid/liquid mixture, including systems employing either the solid phase antibody or solid phase double antibody (DASP) techniques. For example, one phase, usually the solid phase, may comprise bound antigen, the other phase the corresponding free antigen, and the solid phase may be separated from the supernatant liquid by the method of the invention. Such a bound solid phase may comprise any suitable solid phase material, preferably in particulate form and includes those which are well known in the radioimmunoassay filed. For example Sepharose or Sephadex particles have been found to be particularly satisfactory for the purposes of the present invention. The liquid phase, normally comprising the free antigen, is usually in the form of an aqueous solution.

Thus in a preferred embodiment the present invention comprises a binding assay separation technique for the separation of a mixture of a solid phase comprising bound antigen or hapten and a liquid phase comprising free antigen or hapten, in which a second liquid, having a density intermediate between those of the solid and liquid phases, is delivered to the mixture to form a discrete layer beneath the mixture, and the solid phase is allowed to separate, conveniently under the action of gravity, into the lower layer of the second liquid.

The liquid which is delivered to form a discrete layer beneath the mixture may be any suitable liquid and thus may be an organic liquid, for instance a water immiscible organic liquid e.g. carbon tetrachloride. More usually, however, the liquid is an aqueous solution of appropriate density. Desirably the liquid has no detrimental chemical or other interactions with the solid or liquid components of the mixture, which in the case of binding assays may comprise relatively unstable proteinaceous materials. Thus for example, suitable liquids include those which are currently used for density gradients for the separation of materials such as proteins and are generally aqueous solutions of highly hydrophilic and electrically non-polar solutes. In particular aqueous solutions of sucrose e.g. about 10 to 20% w/v sucrose solutions, have been found to be particularly satisfactory for use in binding assay separation techniques. Generally also the liquid, in solution form or otherwise, may contain other components as desired.

Advantageously this second denser liquid is delivered to the mixture in a controlled fashion, preferably in a substantially non-turbulent manner to minimize mixing of the denser liquid with the mixture. For instance the dense liquid may be delivered to the mixture preferably towards the base of the mixture, by means of a tubular probe. Thus the invention also includes automated apparatus for delivering the second denser liquid to the mixture in a controlled fashion.

Accordingly apparatus for the separation of solid and liquid components of a mixture for use in the methods of the present invention comprises automated apparatus for delivering a second liquid, of density intermediate between those of the solid and liquid components of the mixture, in a controlled fashion to form a discrete layer beneath said mixture, said automated apparatus comprising a tubular probe for delivering said second liquid and automatic control means for introducing said probe towards the base of said mixture and delivering thereto said second liquid in a substantially non-turbulent manner.

After delivery of the second denser liquid, solid present in the mixture separates, conveniently under the action of gravity, into the lower layer of the denser liquid, and advantageously may be effectively cleaned and contamination by unbound tracer substantially removed as it passes through the second liquid. Subsequently further liquid or liquids of intermediate density and of progressively higher density may be delivered to form a further discrete layer or layers below the initial layer of the second dense liquid, and the addition of further layers of denser liquid is particularly desirable when the solid is required in a high state of purity, e.g. when it is required that there be minimal contamination of the solid phase "bound" fraction by "free" labelled antigen or hapten.

After separation of the solid and liquid components of the mixture the supernatant liquid, alone or together with solid-free dense liquid, may be removed and further treated or discarded as desired. Similarly as for the delivery of liquid to the mixture, the removal of liquid is advantageously carried out in a controlled fashion, preferably in a substantially non-turbulent manner.

Thus in a further aspect the present invention comprises a method for the separation of solid and liquid components of a mixture in which a second liquid, having a density intermediate to those of the solid and liquid components of the mixture, is delivered to the mixture to form a discrete layer beneath the mixture, solid is allowed to separate, conveniently under the action of gravity, into the lower layer of the second liquid, and the supernatant liquid is removed. The invention also includes apparatus for removal of liquid in a controlled fashion for use in the method as above either separately or in combination with the aforementioned apparatus for delivery of liquid. Similarly as for the automated apparatus for delivering the second denser liquid the apparatus for removal of supernatant liquid may also be readily automated. For instance the liquid may be sucked up, preferably from the top of the layers of liquid by means of a catheter or other tubular probe. Thus in an automated system there may be a plurality of tubular probes for delivery and removal of liquids, including wash liquid if desired, arranged in an appropriate gantry beneath which samples of mixture pass on a suitable conveyor, the whole typically in the form of an endless belt or other similar discrete sample system. In a particularly preferred embodiment liquid is sucked from just beneath the surface and the tubular probe is advanced to keep in step with the fall in the liquid level, and in this way the surface layer is progressively removed in a "bacon slicer" fashion preferably with minimal stirring of the liquid and solid beneath. In an automated system pneumatic piston and cylinder devices have been found to be highly satisfactory for lowering and raising the tubular probes to and from sample containers, though other similar devices may be employed. These devices may conveniently be used in combination with a suitable sensing device, such as a photo-cell, which senses the arrival of a sample container and activates the device.

Also the apparatus may include sample containers modified for use in the method of the invention. For instance the sample container may be provided with a side arm or overflow means by which supernatant liquid may be removed. Alternatively the sample container may be in the form of two side by side compartments having a weir or barrier between them over which supernatant liquid can flow, thus effecting separation of the solid and liquid components of the mixture between the two compartments of the container.

The type of labelling tracer which is used in a binding assay may influence the particular procedure or apparatus employed. Suitable labels include radionuclides, both $\gamma$-emitting tracers such as radioactive iodine ($I^{125}$) and $\beta$-emitting tracers such as Tritium ($H^3$), and in these cases it is desirable to monitor the tracers in the solid phase. Thus for example, in the case of $\gamma$-emitting tracers, after separation of the solid into the lower liquid layer the sample container may be introduced to a well-type counter for direct 'counting' of the radioactivity. The supernatant liquid is preferably drawn off before introduction of the sample to the counter, though an appropriately screened and modified counter may be employed.

$\beta$-emitting tracers are usually monitored by liquid scintillation techniques and thus either the tracer may be dissociated from the solid phase into solution with the liquid scintillator, or the solid phase itself may be held in suspension in the liquid scintillator. Alternatively the $\beta$-emitting tracer may be monitored as a component of supernatant liquid phase. In a preferred embodiment, however, the solid phase incorporating $\beta$-emitting tracer is allowed to separate into the lower layer of the second liquid, supernatant liquid together with solid-free dense liquid is removed, and a liquid scintillator containing a thixotropic agent is then jetted into the remaining liquid and rapidly gelantinises to hold the solid suspended within it. Also the dense liquid itself may comprise a gelling agent such that the lower liquid layer slowly gelantinises becoming solidified only after the solid has precipitated into it, and the supernatant liquid may then be drawn off.

Alternatively non-radionuclide labelling may be used, such as chromophore or fluorescent labels attached to the antigen or hapten. Also enzyme or catalyst labels, such as those which may be used subsequently to generate a detectable signal such as a colored compound, may be employed. Generally these non-radionuclide labels are monitored by techniques such as colourimetry, spectrophotometry or fluorimetry, in which case case it may be desirable to determine the labelled material as a component of the supernatant liquid. Thus monitoring may be carried out with the supernatant liquid in situ in the sample container above the layer of dense liquid or alternatively the supernatant liquid may be drawn off into a separate container for monitoring or further treatment. For example the supernatant liquid itself may not initially contain the substance which is monitored and it may be necessary to carry out some transformation on or by the supernatant e.g. to produce a colored compound, before the labelled material can be monitored.

The invention is further illustrated in the following examples and description which refer to the accompanying diagrams in which.

EXAMPLE 1
RADIOIMMUNOASSAY FOR PLATELET β THROMBOGLOBULIN (BTG)

After primary incubation with $^{125}I$ BTG, 1 ml aliquots of standard BTG of known concentrations in the range from 0.2 to 25.6 g/ml are incubated in 75 × 17 mm sample tubes with an antibody to BTG coupled to Sepharose 4B. After incubation the Sepharose 4B and supernatant are separated by the method of the invention as follows.

1 ml of diluent is added to each sample tube followed by 6 ml of 10% w/v sucrose in water. The sucrose solution is added over a period of about 15 seconds through a stainless steel probe by means of a peristaltic pump. The outlet of the probe is positioned about 0.5 cm from the bottom of the sample tube, and the sucrose solution forms a discrete layer beneath the incubate. In this way the sucrose addition is carried out in a substantially non-turbulent manner. The sample tubes are then left to stand for about 60 minutes during which time the Sepharose 4B together with bound BTG settles out of the incubate into the sucrose solution forming a deposit at the bottom of each tube.

Figure 1:
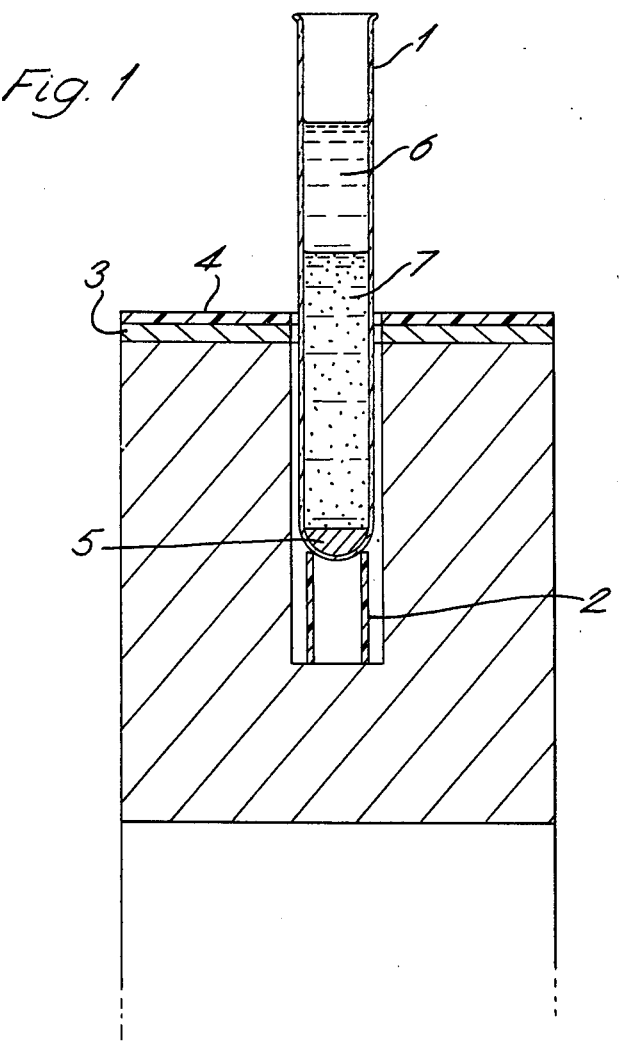
FIG. 1 represents a modified radioactive counter holding a sample container in which the solid and liquid components of a mixture have been separated by the method of the present invention.

Each sample tube, in turn, is then placed in an auto-γ counter (Wallac Instruments Ltd) modified as shown in FIG. 1 and counted for a period of 49.9 seconds (this being the period required to yield 10,000 counts from the total amount of $^{125}I$-BTG added to each tube). The sample tubes are then left to stand for a further 16 hours, and each sample tube is again counted. The results obtained are given in Table I, dividing the counts obtained by 100 giving the results in terms of the percentage of the total $^{125}I$-BTG which has been bound in each case. The two sets of results are in good agreement demonstrating the remarkable stability of the sucrose/diluent interface.

Table 1

| Amount of Standard BTG (μg) | Counts (in 49.9 sec) | |
|---|---|---|
| | A after 1 hr. standing | B after 17 hrs. standing |
| 0 | 4617) x × (% bound) | 4584 x × (% bound) |
| 0 | 4492) | 4474) |
| | 45.7 | 45.1 |
| 0 | 4581) | 4503) |
| 0 | 4599) | 4496) |
| 0.2 | 3061) | 3110) |
| | 32.3 | 31.3 |
| 0.2 | 3409) | 3154) |
| 0.4 | 2657) | 2059) |
| | 27.2 | 27.3 |

Table 1-continued

| Amount of Standard BTG (μg) | Counts (in 49.9 sec) | |
|---|---|---|
| | A after 1 hr. standing | B after 17 hrs. standing |
| 0.4 | 2784) | 2816) |
| 0.8 | 2117) | 2059) |
| | 22.0 | 20.9 |
| 0.8 | 2286) | 2129) |
| 1.6 | 1469) | 1451) |
| | 15.1 | 14.5 |
| 1.6 | 1552) | 1447) |
| 3.2 | 1103) | 979) |
| | 10.4 | 9.9 |
| 3.2 | 986) | 1001) |
| 6.4 | 706) | 650) |
| | 7.1 | 6.6 |
| 6.4 | 721) | 665) |
| 12.8 | 465) | 440) |
| | 4.8 | 4.5 |
| 12.8 | 495) | 458) |
| 25.6 | 346) | 337) |
| | 3.5 | 3.3 |
| 25.6 | 357) | 321) |
| Controls without antibody | 133) | 160) |
| | 1.5 | 1.5 |
| | 180) | 149) |

With reference to FIG. 1 the γ-counter has a well type detector into which the sample tube 1 enters. The detector is modified by placing a 2.5 cm length of plastic tube 2 in the bottom of the well and adding an annular disc 3 of lead screening material beneath customary annular plastic disc spill shield 4. In such an arrangement the source which is to be counted, the bound $^{125}I$ BTG linked to the deposit of Sepharose 4B 5 at the bottom of the tube 1, is well within the detector. The free $^{125}I$ BTG present in the 2 ml layer of aqueous incubate 6 is separated from the detector by the intervening 6 ml layer 7 of 10% w/v sucrose solution, and also the detector is shielded to a large extent against stray radiation from the free fraction by the disc 3 of lead screening material. For all intents and purposes the detector "sees" only radiation from the bound and not from the free fraction.

EXAMPLE 2
RADIOIMMUNOASSAY FOR HUMAN FOLLICLE STIMULATING HORMONE (hFSH)

A comparison of the separation of "bound" from "free" $^{125}I$-FSH by conventional centrifuge techniques and by the technique of the present invention is carried out as follows. After incubation of aliquots of the tracer ($^{125}I$-FSH) and primary antibody (guinea pig anti-hFSH) a solid phase second antibody (rabbit anti-guinea pig γ globulin serum coupled to Sepharose 4B) is added to each incubate giving a total volume of 0.5 ml in each tube, and the tubes are agitated for 30 minutes. Control tubes containing tracer and solid phase second antibody but no primary antibody are also prepared for the purposes of comparison. The tubes are then divided into three groups (A, B and C) and further treated as follows.

(A) 6 ml of diluent is added to each tube in this group and the diluent is thoroughly mixed with the incubate. The tubes are then centrifuged at 2000 g for 5 minutes and the supernatant liquid discarded. A further 6 ml of diluent is added to each tube, the diluent mixed with the deposit, centrifugation repeated, the supernatant again discarded, and the tubes are then counted using the Wallac auto-γ counter as in Example 1 though without the modifications as in FIG. 1.

(B) 0.5 ml of diluent is added to each tube in this group and the diluent thoroughly mixed with the incubate. 1.2 ml of a 10% w/v aqueous solution of sucrose is then immediately added to each tube using a stainless steel probe and peristaltic pump as described in Example 1. The tubes are left to stand for 10 minutes during which time the solid bound Sepharose phase settles under the action of gravity into the sucrose layer. 1.2 ml of liquid (i.e. 1 ml of upper aqueous layer and the interface and about 0.2 ml of the sucrose) is then removed from the top of each tube by means of a glass tube connected to a water pump. The contents of each tube are then counted by placing them in an unmodified counter as in A above.

(C) The tubes in this group are initially treated as are the tubes in Group B. Prior to counting however, 1.2 ml of 20% w/v aqueous sucrose solution is layered beneath the suspension of Sepharose in 10% sucrose. The tubes are then left to stand for a further 10 minutes, the Sepharose settling under the action of gravity into the layer of 20% sucrose, and 1.2 ml of liquid is removed from the top of each tube. The delivery and removal of liquids is carried out in the same way as in Group B. The tubes are then counted using an unmodified counter as above, the results obtained being given in Table 2 below.

Table 2

| | "O"standards | Controls |
|---|---|---|
| Group A(centrifuged controls) | 36.9% Bond | 2.9% Bond |
| Group B in situ system 1 wash | 36.9% B | 1.8% B |
| Group C in situ system 2 washes | 34.3% B | 0.8% B |

As can be clearly seen from Table 2 the results obtained from Group B (1 wash with a single 10% sucrose solution) are in excellent agreement with those obtained by the conventional centrifugation technique. Also the results obtained from Group C (1 wash with 10% sucrose and 1 wash with 20% sucrose) show a small decrease, illustrating how a further sucrose wash may decrease the effect of non-specific intrusion of "free" $^{125}$I-FSH into the "bound" Sepharose component.

Figure 2:
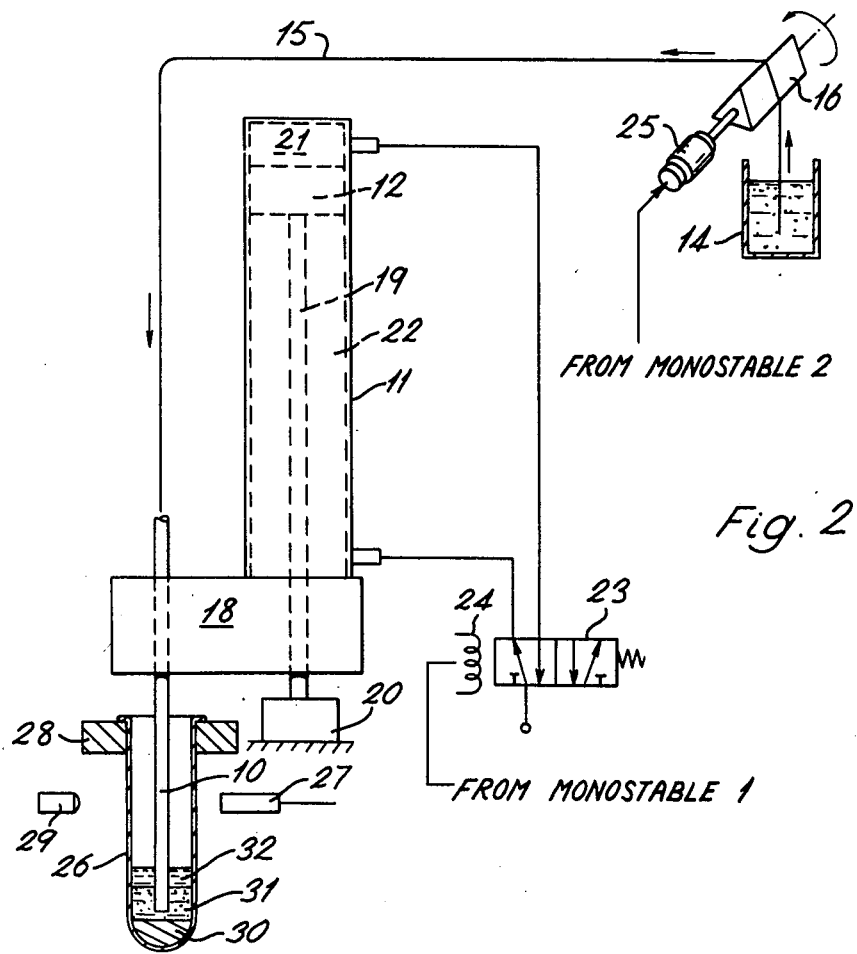
FIG. 2 presents automated apparatus in accordance with the present invention for delivery of a second denser liquid to a solid-liquid mixture.
Figure 3:
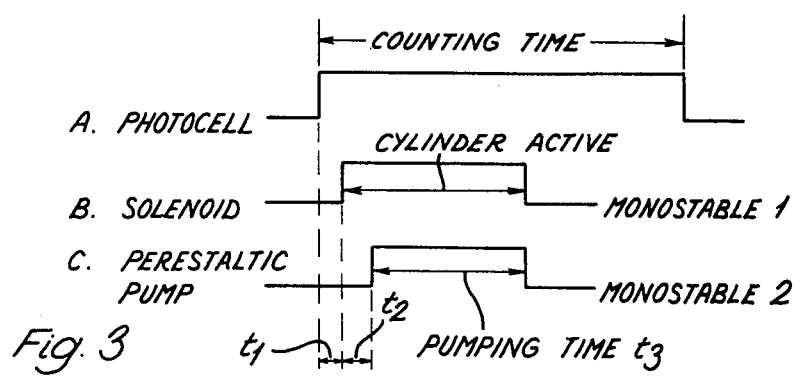
FIG. 3 represents diagrammatically the pulse-time pattern of the automatic control means of the apparatus of FIG. 2.
Figure 4:
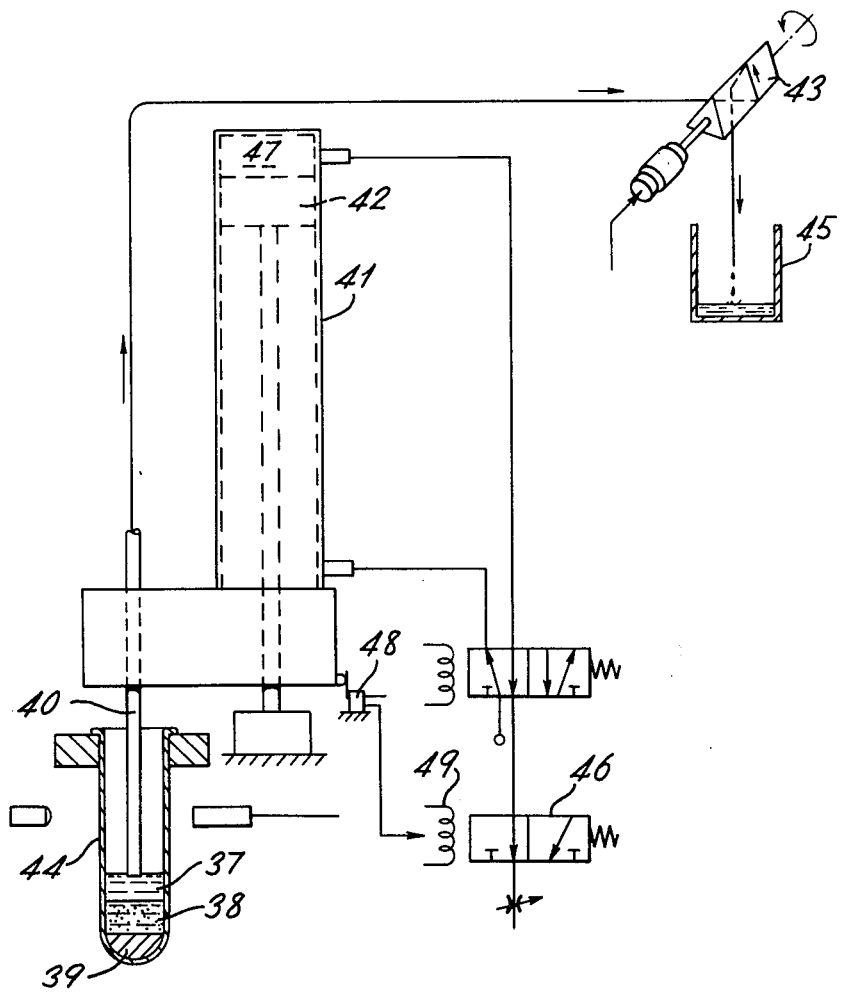
FIG. 4 represents automated apparatus in accordance with the present invention for removal of supernatant liquid from sample containers after separation of the solid and liquid components of mixtures by the method of the invention.

The addition of a dense second liquid to the solid-liquid-mixture and subsequent removal of supernatant liquid as outlined in Example 2 may be readily automated, and appropriate automated apparatus is now described, by way of further illustration of the invention, with reference to the accompanying diagrams FIGS. 2, 3 and 4.

FIG. 2 shows automated apparatus for addition of sucrose solution to a solid phase double antibody (DASP) aqueous mixture comprising a tubular stainless steel probe 10 which may be automatically lowered and raised by means of a pneumatic cylinder 11 and piston 12 device to introduce the probe 10 to sample containers 26. The probe 10 is supplied with sucrose solution from a reservoir 14 through a length of flexible plastic tubing 15 by means of peristaltic pump 16. The probe 10 is located in a seating provided in a side arm 18 of the pneumatic cylinder 11, which is vertically slidable on its piston 12, which in turn is firmly held in fixed position by a connecting rod 19 passing through a seal in the lower end of the cylinder 11 and attached at its end to a firm base 20. The piston 12 divides the cylinder 11 into two compartments 21 and 22 each supplied separately with compressed air from a five port, solenoid operated, spring return, pneumatic valve 23. The solenoid 24 for the valve 23 and the motor 25 for the peristaltic pump 16 are each separately connected to suitable monostable time delay circuits (not shown) which supply electric pulses for appropriate periods of time and at appropriate points in time to lower the probe into the sample tube 26 and deliver the required quantity of sucrose solution. The monostable time delay circuits are activated by a photocell 27 located at the sucrose addition station.

In practice a sample tube 26 containing mixture is conveyed towards the sucrose addition station by the conveyor 28, and on arrival the tube 26 intervenes between the light bulb 29 and photo-cell 27 activating the monostable time delay circuits. The pulse-time patterns of these circuits and of the photocell 27 are illustrated diagrammatically in FIG. 3, wherein A represents the photo-cell circuit, B the first monostable circuit which activates the valve 23 and C the second monostable circuit which activates the peristaltic pump motor 25. Thus after an initial time gap $t_1$ the first monostable circuit switches on, activating the solenoid 24, moving the valve 23 and diverting the supply of compressed air from compartment 21 to compartment 22 of the cylinder 11 which causes the probe 10 to lower into the sample tube 26. The initial time delay $t_1$ is required as a finite time will elapse between sensing of the edge of the tube 26 by the photo-cell 27 and the tube 26 taking up its correct position vertically beneath the probe 10. After a further time delay $t_2$ the second monostable circuit switches on activating the peristaltic pump motor 16, and sucrose solution is delivered in a substantially non-turbulent manner via the probe 10 to the mixture in the sample tube 26. After a further period of time $t_3$ both monostable circuits switch off. The solenoid 24 is deactivated and the spring return moves the valve 23 back to its original position diverting compressed air into compartment 21 of the cylinder 11 which causes the probe 10 to be raised from the sample tube 26. Also the current to the pump motor 25 is switched off and sucrose solution ceases to be delivered to the mixture. The solid phase double antibody (DASP) material 31 then settles under the action of gravity out of the mixture through the layer of sucrose solution 31 to form a deposit 30 at the bottom of the sample tube 26. In this fashion the DASP material is separated from the supernatant liquid 32.

Similarly FIG. 4 shows automated apparatus for removal of supernatant liquid 37 from above a layer of dense sucrose solution 38 and a deposit of separated DASP material 39, and similarly comprises a tubular stainless steel probe 40 which may be automatically raised and lowered by means of a free vertically slidable cylinder 41 and fixed piston 42 pneumatic device. The supernatant extraction apparatus is similar in construction and design to the sucrose addition apparatus of FIG. 2. The peristaltic pump 43, however, is arranged to pump liquid from the sample containers 44 to a waste reservoir 45, and need not be connected to an on/off switching device but may be left to run continuously. Also the extraction system is provided with a secondary solenoid operated, spring return, three port, pneumatic valve 46 which is used to restrict the exhaust of air from compartment 47 of cylinder 41 thus controlling the velocity at which probe 40 is lowered into the sample tube 44. This further valve 46 is activated by a microswitch 48, or other suitable switching device, arranged to switch on the solenoid 49 controlling valve 46 when the probe 40 has just entered beneath the surface of supernatant 37 in the tube 44. In this way the probe makes an initial fast approach into the tube 44 until it reaches just below the fluid surface and thereafter the downward velocity of the probe 40 is reduced keeping it just below the surface as extraction takes place. Such an arrangement has been found to be particularly desirable for removal of supernatant liquid in a substantially non-turbulent manner, causing minimal stirring of the sucrose and DASP material.

Otherwise the arrangement of the extraction apparatus and mode of lowering and raising the probe 40 is similar to that of the sucrose addition apparatus of FIG. 2. The apparatuses of FIGS. 2 and 4 may be used either separately or in combination in automated analytical systems according to the present invention.

It will be appreciated, however, that the automatically controlled means for introducing dense liquid and removing supernatant, as outlined in the foregoing description, are only examples of the devices which might be used and other devices besides pneumatic devices are included within the scope of the invention.

I claim:

1. A separating and analyzing method including separating solid and liquid components of a mixture comprising;
   delivering to the mixture a second liquid, having a density intermediate between those of the solid and liquid components of the mixture, to form a discrete layer above or below the mixture;
   allowing the solid to separate into the layer of the second liquid; and, automatically analyzing the solid or liquid components.

2. A method according to claim 1, in which the second liquid forms a discrete layer beneath the mixture and the solid separates under the action of gravity into the layer of the second liquid.

3. A method according to claim 2, in which further liquid or liquids of intermediate density and progressively higher density are delivered to form a further discrete layer or layers below the initial layer of the second dense liquid.

4. A method according to claim 2, in which, after separation of the solid and liquid components of the mixture, supernatant liquid, alone or together with solid-free dense liquid, is removed and further treated or discarded as desired.

5. A method according to claim 4, in which the removal of liquid is carried out in a controlled fashion in a substantially non-turbulent manner and in which the second liquid of intermediate density comprises an aqueous solution of highly hydrophilic and electrically non-polar solute.

6. A method according to claim 1 in which the automatic analyzing step includes a binding assay technique, and in which the mixture consists of solid phase comprising bound antigen or hapten and liquid phase comprising free antigen or hapten.

7. A method according to claim 4, in which the solid and liquid components of the mixture comprise a suitable labelling tracer.

8. A method according to claim 5, in which the labelling tracer comprises a radionuclide tracer.

9. A method according to claim 7, in which, subsequent to separation of the solid and liquid components of the mixture, the labelling tracer is monitored in the solid phase.

10. A method according to claim 1, in which the second liquid of intermediate density comprises an aqueous solution of a highly hydrophillic and electrically non-polar solute.

11. A method according to claim 4, in which the second liquid of intermediate density comprises an aqueous sucrose solution.

12. A method according to claim 4, in which the second liquid of intermediate density is delivered to the mixture in a controlled fashion and a substantially non-turbulent manner.

13. Apparatus for the separation of solid and liquid components of a mixture comprising an automated apparatus for delivering a second liquid having ab initio a density intermediate between those of the solid and liquid components of the mixture, in a controlled fashion to form a discrete layer beneath said mixture, said automated apparatus for delivering a second liquid comprising a tubular probe for delivering said second liquid and automatic control means for introducing and advancing said probe towards the base of said mixture and delivering thereto said second liquid in a substantially non-turbulent manner in which the means for introducing and advancing the tubular probe comprises a pneumatic cylinder and piston device.

14. Apparatus for the separation of solid and liquid components of a mixture according to claim 13 which further comprises an automated apparatus for removal of supernatant liquid in a controlled fashion from above a layer of a second denser liquid into which the solid component has separated, said automated apparatus for removal of supernatant liquid comprising a tubular probe through which said supernatant liquid is removed, means for removing said supernatant liquid, and automatic control means for introducing said probe just beneath the surface of said supernatant liquid and advancing said probe to keep in step with the fall in the liquid level.

15. Apparatus according to claim 13, which further comprises combined means for delivery of a second dense liquid and removal of supernatant liquid.

* * * * *